(12) United States Patent
Chauhan et al.

(10) Patent No.: US 9,101,138 B2
(45) Date of Patent: Aug. 11, 2015

(54) METHODS AND COMPOSITIONS UTILIZING LACTAMS DERIVED FROM CAMPHOR, VERBENONE OR CAT THYME OIL FOR REPELLING BLOOD-SUCKING AND BITING INSECTS, TICKS AND MITES

(71) Applicants: The United States of America, as represented by the Secretary of Agriculture, Washington, DC (US); Chemveda Life Sciences Inc., San Diego, CA (US)

(72) Inventors: Kamlesh R. Chauhan, Laurel, MD (US); Bheema R. Paraselli, San Diego, CA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 14 days.

(21) Appl. No.: 13/826,431

(22) Filed: Mar. 14, 2013

(65) Prior Publication Data

US 2014/0275034 A1    Sep. 18, 2014

(51) Int. Cl.
| | |
|---|---|
| *A01N 43/46* | (2006.01) |
| *C07D 507/00* | (2006.01) |
| *A01N 43/16* | (2006.01) |
| *A01N 43/42* | (2006.01) |
| *A01N 35/06* | (2006.01) |
| *A01N 35/08* | (2006.01) |

(52) U.S. Cl.
CPC ............. *A01N 43/46* (2013.01); *A01N 35/06* (2013.01); *A01N 35/08* (2013.01); *A01N 43/16* (2013.01); *A01N 43/42* (2013.01)

(58) Field of Classification Search
CPC ...................................... A01N 43/46
See application file for complete search history.

(56) References Cited

PUBLICATIONS

Suginome, H., et al. "Photoinduced Molecular Transformations. Part 119. Photochemical Nitrogen Insertion into Bicyclo[2.2.1]heptanones; The Photochemistry of Oximes of (+)-Fenchome and (+)-Camphor." J. Chem. Soc. Perkins Trans. 1 (1991), pp. 917-921.*
Nagai, S., et al. "Bridgehead Nitrogen Heterocycles. Synthesis of Methanoazepines Fused with Tetrazole 1,2,4-Triazole and 1,2,4-Triazine." Heterocycles. (1986), vol. 24, No. 4, pp. 907-912.*
Polonski, T., et al. "Conformational properties and chiroptical spectra of lactams and thiolactams with 2-azabicyclo[2.2.1]heptane, 2- and 3-azabicyclo[32.1]octane skeletons." Tetrahedron: Asymmetry. (1999), vol. 10, pp. 2591-2604.*
Zahn, D.K. et al., Identification, Synthesis, and Bioassay of a Male-Specific Aggregation Pheromone from the Harlequin Bug, *Murgantia histrionica*, J. Chem. Biol., 2008, vol. 34, pp. 238-251.

* cited by examiner

*Primary Examiner* — Noble Jarrell
*Assistant Examiner* — John S Kenyon
(74) *Attorney, Agent, or Firm* — John D. Fado; G. Byron Stover

(57) ABSTRACT

A method for repelling blood-sucking and biting insects, ticks and mites involving treating an object or area with a blood-sucking and biting insects, ticks and mites repelling effective amount of camphor lactams, verbenone lactams, dolicholactams, dolicholactone, and their precursors, and mixtures thereof, and optionally a carrier.

15 Claims, 4 Drawing Sheets

METHODS AND COMPOSITIONS UTILIZING LACTAMS DERIVED FROM CAMPHOR, VERBENONE OR CAT THYME OIL FOR REPELLING BLOOD-SUCKING AND BITING INSECTS, TICKS AND MITES

BACKGROUND OF THE INVENTION

Disclosed are methods for repelling blood-sucking and biting insects, ticks and mites involving treating an object or area with a blood-sucking and biting insects, ticks and mites repelling effective amount of at least one compound selected from

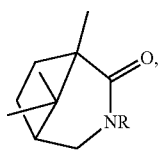
1

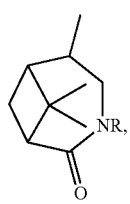
2

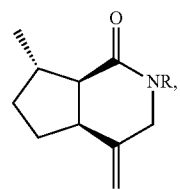
3

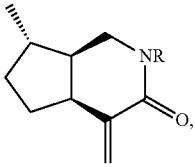
4

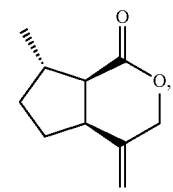
5

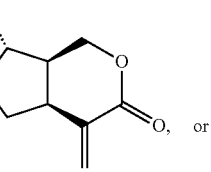
6 or

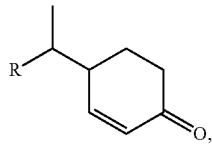
7 and mixtures thereof; where R is H, C1 to C10 alkyl (preferably C1-C5, more preferably C1-C3), or C1 to C10 alkenyl (preferably C1-C5, more preferably C1-C3); and optionally a carrier. Also disclosed are compositions containing at least one compound selected from

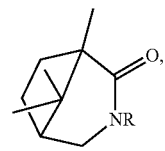
1

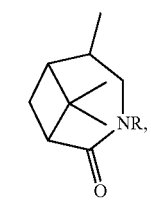
2

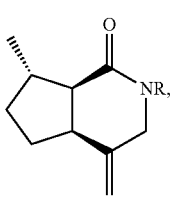
3

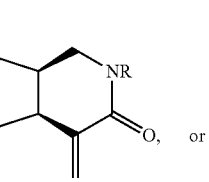
4 or

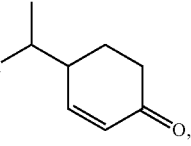

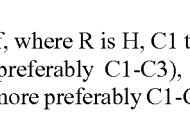
7 and mixtures thereof, where R is H, C1 to C10 alkyl (preferably C1-C5, more preferably C1-C3), C1 to C10 alkenyl (preferably C1-C5, more preferably C1-C3), and optionally a carrier.

Repellent substances generally cause insects to be driven away from, or to reject, otherwise insect-acceptable food sources or habitats. About 85% of insect repellent sales in the United States are for insect repellents containing N,N-diethyl-m-toluamide (DEET) as their primary active ingredient. Although DEET is an effective repellent, it possesses an unpleasant odor and imparts a greasy feeling to the skin. In addition, concerns have been raised as to its safety, particularly when applied to children (Briassoulis, G., et al., Human & Experimental Toxicology, 20(1): 8-14 (2001)). Another disadvantage of DEET is that it dissolves or mars many plastics and painted surfaces.

Because of the above limitations, DEET-free products with repellent activity are being sought. New candidate repellents should possess a desirable balance of properties and will preferably reach or exceed the positive properties of DEET, and/or not suffer from its negative properties (Hollon, T., The Scientist, Jun. 16, 2003, pages 25-26). Potential substitutes for DEET should desirably then exhibit a combination of excellent repellency, high residual activity, and low toxicity to humans (or pets) and the environment. Any candidate to replace DEET should exhibit repellency to a wide variety of insects considered noxious by humans, including, but not limited to, biting insects, wood-boring insects, noxious insects, household pests, and the like. In addition, there is increasing demand for repellent compounds that can be obtained from, or synthesized from, natural plant materials and that are pleasant to use.

Many plant species produce essential oils (aromatic oils) which are used as natural sources of insect repellent and fragrant chemicals (Hay, R. K. M., and K. P. Svoboda, Botany, In Volatile Oil Crops: Their biology, chemistry and production, R. K. M. Hay and P. G. Waterman (eds.), Longman Group UK Limited (1993)). Plants of the genus *Nepeta* (catmints) produce an essential oil that is very rich in a class of mono terpenoid compounds known as iridoids (Inouye, H., Methods in Plant Biochemistry, 7:99-143 (1991)), more specifically the cyclopentanoid nepetalactones (Clark, L. J., et al., The Plant Journal, 11: 1387-1393 (1997)) and derivatives. Studies of the repellency of catnip oil (predominantly nepetalactone) showed that it was repellent towards a number of insect species (e.g., mosquitoes, cockroaches, ants) on short-term exposure but not to a number of other species (e.g., agriculture pests such as stink bugs, beetles, etc.) (Eisner, T., Science, 146: 1318-1320 (1964)). Similarly plants in the cat thyme family contain volatile iridoid monoterpenes and have shown a similar spectrum of semiochemistry (Tucker and Tucker, Economic Botany, 42, 214-231 (1988)).

U.S. Pat. No. 4,663,346 discloses insect repellants containing bicyclic iridoid lactones (e.g., iridomyrmecin). U.S. Pat. No. 4,869,896 discloses use of these bicyclic iridoid lactone compositions in potentiated insect repellent mixtures with DEET. U.S. Pat. No. 6,524,605 discloses insect repellents containing nepetalactones derived from the catmint plant *N. cataria*. U.S. Patent Application 2004/0127553 discloses that dihydronepetalactones have been identified as an effective insect repellent compound. U.S. Pat. No. 7,067,678 discloses that 3-substituted dihydronepetalactones are insect repellants. However, there continues to be a need for additional commercially and economically viable better alternatives to DEET with efficacy, safety profile and less vapor pressure.

SUMMARY OF THE INVENTION

Disclosed are methods for repelling blood-sucking and biting insects, ticks and mites involving treating an object or area with a blood-sucking and biting insects, ticks and mites repelling effective amount of at least one compound selected from

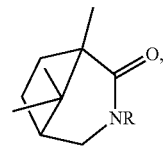
1

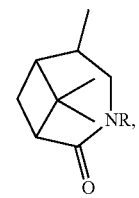
2

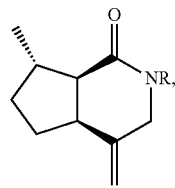
3

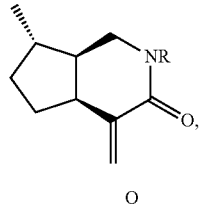
4

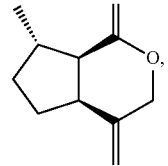
5

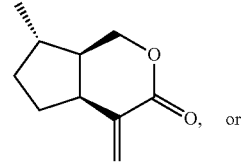
6

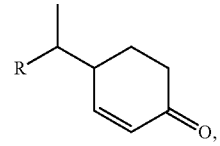
7 and mixtures thereof, where R is H, C1 to C10 alkyl (preferably C1-C5), or C1 to C10 alkenyl (preferably C1-C5); and optionally a carrier.

Also disclosed are compositions comprising at least one compound selected from

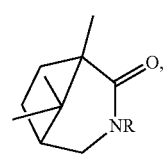
1

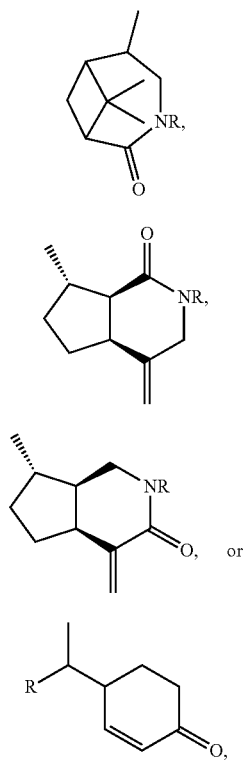

and mixtures thereof, where R is H, C1 to C10 alkyl (preferably C1-C5, more preferably C1-C3), or C1 to C10 alkenyl (preferably C1-C5, more preferably C1-C3), and optionally a carrier.

DETAILED DESCRIPTION OF THE INVENTION

Figure 1:
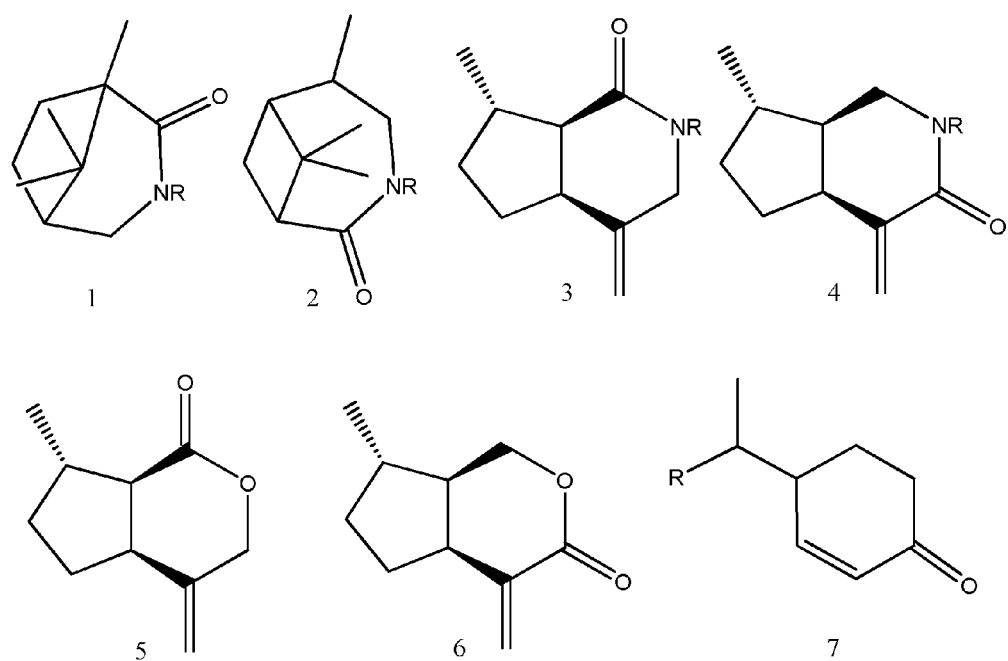
FIG. 1 shows the chemical formulas of compounds as described below.
Figure 2:
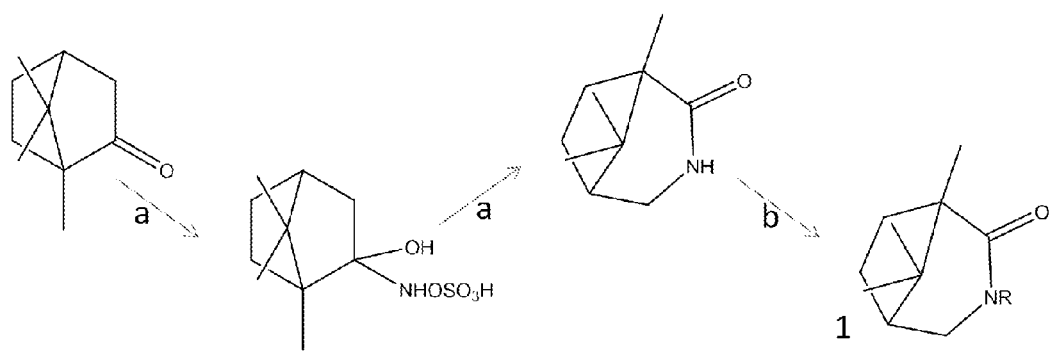
FIG. 2 shows synthesis of lactams 1 as described below; reagents and conditions: (a) hydroxylamine-O-sulphonic acid in 95% formic acid, 0° C. to reflux, 6 hrs, (b) NaH, 0° C. RI, in dry THF
Figure 3:
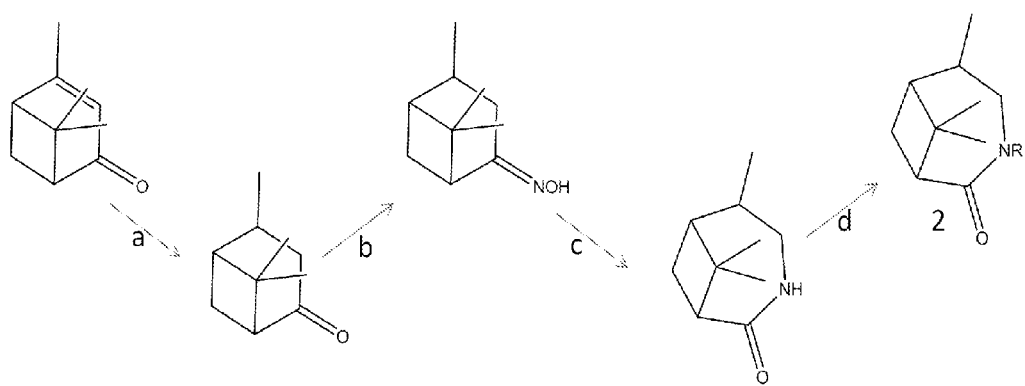
FIG. 3 shows synthesis of lactams 2 as described below; reagents and conditions: (a) Pd\C—H$_2$ (b) NH$_2$OH—HCl, (c) NaH, 0° C. RI, in dry THF
Figure 4:
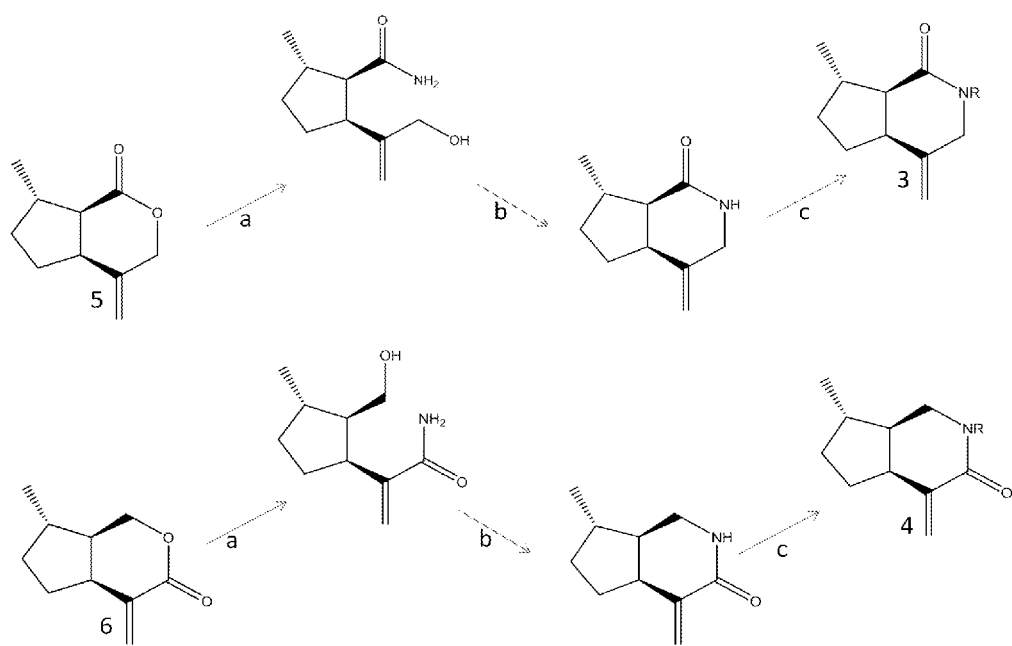
FIG. 4 shows synthesis of dolicholactams 3 and 4 as described below; reagents and conditions: (a) aq. NH$_4$OH, concentrate H$_2$SO$_4$, 0° C., (b) cat TsOH, azeotropic distillation, (c) NaH, 0° C. RI, THF

Compositions are disclosed for repelling blood-sucking and biting insects, ticks and mites, containing at least one compound selected from camphor lactams, verbenone lactams, dolicholactams, dolicholactone, or their precursors, and mixtures thereof, and optionally a carrier.

Methods are disclosed for repelling blood-sucking and biting insects, ticks and mites from an object (e.g., mammals such as humans) or area (e.g., a surface such as human skin), involving treating (or exposing) the object or area with the above composition (optionally including a carrier material or carrier).

The terms "object" or "area" as used herein include any place where the presence of target pests (e.g., mosquitoes) is not desirable, including any type of premises, which can be out-of-doors, such as in gardens, lawns, tents, camping bed nets, camping areas, and so forth, or indoors, such as in barns, garages, commercial buildings, homes, and so forth, or any area where pests are a problem, such as in shipping or storage containers (e.g., bags, boxes, crates, etc.), packing materials, bedding, and so forth; also includes the outer covering of a living being, such as skin, fur, hair, or clothing. Thus the method includes dispensing the compounds described herein into the environment in vapor form (e.g., an aerosol) preferably using devices that allow a slow sustained release of these compounds into the environment from a sealed canister.

The compositions and compounds can also be used for repelling harmful or troublesome blood-sucking and biting insects, ticks and mites including mosquitoes (for example *Aedes*, *Culex* and *Anopheles* species including but not limited to Tiger mosquitoes, *Aedes aboriginis*, *Aedes aegypti*, *Aedes albopictus*, *Aedes cantator*, *Aedes sierrensis*, *Aedes sollicitans*, *Aedes squamiger*, *Aedes sticticus*, *Aedes vexans*, *Anopheles quadrimaculatus*, *Culex pipiens*, and *Culex quinquefasciatus*), sand flies (for example *Phlebotomus* and *Lutzomyia* species), bed bugs (for example *Cimex lectularius*), owl gnats (*Phlebotoma*), blackfly (*Culicoides* species), buffalo gnats (*Simulium* species), biting flies (for example *Stomoxys calcitrans*), tsetse flies (*Glossina* species), horseflies (*Tabanus*, *Haematopota* and *Chrysops* species), house flies (for example *Musca domestica* and *Fannia canicularis*), meat flies (for example *Sarcophaga carnaria*), flies which cause myiasis (for example *Lucilia cuprina*, *Chrysomyia chloropyga*, *Hypoderma bovis*, *Hypoderma lineatum*, *Dermatobia hominis*, *Oestrus ovis*, *Gasterophilus intestinalis* and *Cochliomyia hominovorax*), bugs (for example *Cimex lectularius*, *Rhodnius prolixus* and *Triatoma infestans*), lice (for example *Pediculus humanus*, *Haematopinus suis* and *Damalina ovis*), louse flies (for example *Melaphagus orinus*), and fleas (for example *Pulex irritans*, *Cthenocephalides canis* and *Xenopsylla cheopis*), sand fleas (for example *Dermatophilus penetrans*), and blood-feeding ticks include (for example, *Ornithodorus moubata*, *Ixodes ricinus*, *Ixodes scapularis*, *Boophilus microplus*, *Amblyomma americanum*, and *Amblyomma hebreum*, and mites include, for example, *Sarcoptes scabiei* and *Dermanyssus gallinae*).

The compounds, which can be used in undiluted or diluted form, can be converted into formulations customary for repellents. They can be used in all the presentation forms customary in cosmetics and public health pesticides, for example in the form of solutions, emulsions, gels, ointments, pastes, creams, powders, sticks, sprays or aerosols from spray cans.

For use in the non-cosmetic sector, the compounds can be incorporated, for example, into granules, oily spraying agents or slow release formulations.

The formulations are prepared in a known manner by mixing or diluting the compounds with solvents (for example xylene, chlorobenzenes, paraffins, methanol, ethanol, isopropanol or water), carriers (for example kaolins, aluminas, talc, chalk, highly disperse silicic acid and silicates, nanoclays), emulsifying agents (for example polyoxyethylene fatty acid esters, polyoxyethylene fatty alcohol ethers, alkylsulphonates and arylsulphonates) and dispersing agents (for example lignin, sulphite waste liquors and methylcellulose).

The compounds can be mixed with one another in the formulations or can also be used as mixtures with other known active compounds (for example sunscreen agents).

The formulations in general contain between about 0.1 and about 95% (e.g., 0.1-95%) by weight of active compound, preferably between about 0.5 and about 90% (e.g., 0.5-90%).

For protection from mosquitoes, the compounds are generally either applied to human or animal skin, or items of clothing and other objects are treated with the compounds. Preferably, the compounds are dispensed into the environment (e.g., outdoors or indoors) in vapor form (e.g., an aerosol).

The compounds are also suitable as an additive to impregnating agents, for example, textile webs, articles of clothing and packaging materials, and as an additive to polishing, cleaning and window-cleaning agents.

The compositions contain a carrier and the compound. The repellent is generally applied with a carrier component. The carrier component can be a liquid or a solid material. As is known in the art, the vehicle or carrier to be used refers to a substrate such as a gel, polymers, or the like. All of these substrates have been used to release insect repellents and are well known in the art. The carrier or carrier material as used herein is defined as not including a plant (e.g., *Teucrium marum*) or the extract from which a compound is isolated.

The compounds herein are described as repellents because they result in a reduction in the ability of mosquitoes to locate a host, and thus reduce the incidence of biting. Generally, an insect repellant is any compound or composition which deters insects from a host, thus the term "repelling" is defined as causing insects (e.g., *Aedes aegypti*) to make oriented movements away from a source of a chemical repellent (Dethier, V. L., et al., J. Econ. Ent., 53: 134-136 (1960)) but also includes inhibiting feeding by mosquitoes when a chemical is present in a place where mosquitoes would, in the absence of the chemical, feed. Thus the term "repelling" also includes reducing the number of insect (e.g., *Aedes aegypti*) bites on a treated area or object (e.g., mammalian skin which has been treated topically with the compositions or compounds) when compared to the same area or object which is untreated.

The amount of the compound used will be at least an effective amount. The term "effective amount," as used herein, means the minimum amount of the compound needed to reduce the ability of mosquitoes to locate a host and thus reduce the incidence of biting, or to cause mosquitoes to make oriented movements away from a treated area or object (e.g., mammalian skin which has been treated topically with the compound) when compared to the same area or object which is untreated. The term "effective amount," as used herein, also means the minimum amount of the compound needed to reduce the number of insect (e.g., *Aedes aegypti*) bites on a treated area or object (e.g., mammalian skin which has been treated topically with the compound) when compared to the same area or object which is untreated. Effective concentrations of the compound in the compositions may vary between about 0.1 and about 95% (e.g., 0.1-95%) by weight, preferably between about 0.5 and about 90% (e.g., 0.5-90%). Of course, the precise amount needed will vary in accordance with the particular repellent composition used; the type of area or object to be treated; the number of hours or days of repelling needed; and the environment in which the area or object is located. The precise amount of repellent can easily be determined by one skilled in the art given the teaching of this application. For example, one skilled in the art could follow the procedure utilized below.

The compounds may be used with other repellents or mosquito control agents (e.g., insecticides, chemosterilants or the like). When used, these agents should be used in an amount which, as readily determined by one skilled in the arts, will not interfere with the effectiveness of the compound.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

All chemicals used were of reagent grade and obtained from Aldrich Chemical Co. All solvents were obtained from BDH Co. and distilled before used. Melting points were recorded on a Thomas-Hoover melting point apparatus and were uncorrected. Silica gel (230 mesh) was purchased from Merck. Mass spectra were recorded on an Agilent Technologies 6890N with DB-5 column.

Camphor lactams 1: Hydroxylamine-O-sulfonic acid (1.69 g, 15 mmol) in 95% formic acid (10 mL) was added dropwise into a solution of d-Camphor (1.52 g, 10 mmol) in 95% formic acid (10 mL) at 20° C. over 10 minutes. The reaction mixture was refluxed for 6 h then allowed to cool to room temperature, neutralized with 5% sodium hydroxide solution, extracted with chloroform, and dried by $MgSO_4$. Removal of the solvent in vacuo to give crude product which was subjected to liquid chromatography using ethyl acetate:hexanes (15:85) as eluent to give the pure lactam 6 as a white solid (0.73 g, 44% yield); mp 223-224° C. (lit. 231-232° C.); MS m/z 167 (48), 152 (100), 138 (13), 124 (20), 98 (43), 83 (11), 69 (28), 55 (16). Krow, G. R., and S. Szczepanski, Tetrahedron Lett., 21: 4593-4596 (1980); Caamano, O., et al., Tetrahedron, 50: 2175-2182 (1994).

N-propyl camphor lactams 1a: Lactam 1 (167 mg, 1 mmol) was dissolved in freshly-distilled tetrahydrofuran (10 mL) and the solution was ice-cooled to 0° C. Sodium hydride in mineral oil was filtered and washed with hexanes to remove the oil. The oil-free sodium hydride (36 mg, 1.5 mmol) was added into the lactam solution in small portions. The reaction mixture was stirred at for 1 h, treated with iodopropane (255 mg, 1.5 mmol) and allowed to stir for another 1 h. The resulting mixture was neutralized with saturated ammonium chloride, extracted with ether, and dried by $MgSO_4$. Removal of the solvent in vacuo to give crude product which was subjected to liquid chromatography using ethyl acetate:hexanes (15:85) as eluent to give the pure lactam 8 as a yellow oil (185 mg, 88% yield); MS m/z 209 (44), 194 (31), 180 (100), 166 (16), 152 (47), 98 (18), 69 (16), 55 (18). Scialdone, M. A., and A. Y. Liauw, U.S. Patent US 2006/0148842 A1.

Dihydro verbenone lactams 2: Dihydro verbenone was first prepared by hydrogenating the unsaturated (S)-(−)Verbenone (1.5 g, 10 mmol) using 0.5 g of Pd on activated carbon in 25 mL absolute ethanol. After stirring at 24 hrs at room temperature, the mixture was filtered and concentrated to give pure reduced verbenone. Dihydro verbanone (1.44 g, 9.5 mmol) was added to a mixture of hydroxylamine hydrochloride (0.8 g, 11.5 mmol), sodium acetate trihydrate (1.6 g, 11.7 mmol) in 95% ethanol (10 mL) and water (4 mL). The mixture was refluxed for 24 h, poured into a brine solution, and extracted with chloroform. Purification by liquid chromatography on silica gel, using ethyl acetate:hexanes (1:1) as eluent, gave the verbanone oxime 2 as light yellow solid (1.14 g, 72%); mp 64-65° C. (lit. 66-67° C.); MS m/z 167 (18), 152 (31), 150 (34), 124 (48), 110 (27), 83 (100), 67 (20), 55 (52). Wagner, P., et al., J. Am. Chem. Soc., 122: 263-273 (2000); Koval'skaya, S. S., et al., Chem. Nat. Compd., 29: 306-308 (1993).

Dihydro verbenone oxime (300 mg, 0.79 mmol) was dissolved in 0.5 mL of acetonitrile and the solution was ice-cooled to 0° C. Sulfuric acid (0.5 mL) was added dropwise into the solution via syringes over 15 minutes. The reaction mixture was stirred at room temperature for 7 days, worked up by aqueous ammonia, extracted with ether and dried by $MgSO_4$. The crude product was concentrated and subjected to chromatography on silica gel using ethyl acetate:hexanes (15:85) as eluent to give the pure lactam 2 as light yellow solid (210 mg, 70%), mp 89-90° C. (lit. 91° C.); MS m/z 167 (2), 152 (10), 124 (37), 109 (35), 96 (22), 83 (100), 71 (32), 55 (60). Koval'skaya, S. S., et al., Chem. Nat. Compd., 29: 306-308 (1993); Koval'skaya, S. S., et al., Chem. Nat. Compd., 27: 24-27 (1991).

N-propyl dihydro verbenone lactams 2a: The above lactam 2 (334 mg, 2 mmol) was dissolved in freshly-distilled tetrahydrofuran (10 mL) and the solution was ice-cooled to 0° C. Sodium hydride in mineral oil was filtered and washed with hexanes to remove the oil. The oil-free sodium hydride (72 mg, 3 mmol) was added into the lactam solution in small portions. The reaction mixture was stirred at room temperature for 1 h, treated with 2-iodopropane (510 mg, 3 mmol) and allowed to stir at 50° C. for another 1 h. The resulting mixture was neutralized with saturated ammonium chloride, extracted with ether, and dried by $MgSO_4$. Removal of the solvent in vacuo to give crude product which was subjected to liquid chromatography using ethyl acetate:hexanes (15:85) as eluent to give the pure lactam 2a as a yellow oil (284 mg, 68% yield); MS m/z 209 (7), 194 (40), 166 (16), 140 (15), 98 (23), 83 (100), 70 (84), 55 (45). Scialdone, M. A., and A. Y., U.S. Patent 2006/0148842 A1, Jul. 6, 2006.

N-isopropyl camphor lactam 1b: Lactam 1 (334 mg, 2 mmol) was dissolved in freshly-distilled tetrahydrofuran (10 mL) and the solution was ice-cooled to 0° C. Sodium hydride in mineral oil was filtered and washed with hexanes to remove the oil. The oil-free sodium hydride (72 mg, 3 mmol) was added into the lactam solution in small portions. The reaction mixture was stirred at for 1 h, treated with 2-iodopropane (340 mg, 2 mmol) and allowed to stir for another 1 h. The resulting mixture was neutralized with saturated ammonium chloride, extracted with ether and dried by $MgSO_4$. Removal of the solvent in vacuo to give crude product which was subjected to liquid chromatography using ethyl acetate:hexanes (15:85) as eluent to give the pure lactam 5 as a yellow oil (288 mg, 69% yield); MS m/z 209 (12), 194 (25), 180 (48), 166 (24), 140 (26), 83 (100), 70 (71), 55 (48). Scialdone, M. A., and A. Y. Liauw, U.S. Patent 2006/0148842 A1, Jul. 6, 2006.

N-isopropyl ihydro verbenone lactams 2b: Lactam 2 (334 mg, 2 mmol) was dissolved in freshly-distilled tetrahydrofuran (10 mL) and the solution was ice-cooled to 0° C. Sodium hydride in mineral oil was filtered and washed with hexanes to remove the oil. The oil-free sodium hydride (72 mg, 3 mmol) was added into the lactam solution in small portions. The reaction mixture was stirred at room temperature for 1 h, treated with 2-iodopropane (510 mg, 3 mmol) and allowed to stir at 50° C. for another 1 h. The resulting mixture was neutralized with saturated ammonium chloride, extracted with ether and dried by $MgSO_4$. Removal of the solvent in vacuo to give crude product which was subjected to liquid chromatography using ethyl acetate:hexanes (15:85) as eluent to give the pure lactam 7 as a yellow oil (280 mg, 67% yield); MS m/z 209 (29), 194 (100), 180 (13), 166 (9), 152 (19), 98 (7), 81 (8), 58 (23). Scialdone, M. A., and A. Y. Liauw, U.S. Patent US 2006/0148842 A1.

Dolicho-C-lactam 4: A 1 L three-necked round bottom flask was charged with dolicholactone (10 g isolated from cat thyme oil) and 100 ml of aqueous $NH_3$ solution and cooled to 0° C. At the same temperature concentrated $H_2SO_4$ (3 ml) was slowly added dropwise. After the addition was completed, the reaction mixture was heated to reflux at 90° C. for 2 h. As a work-up the reaction was then cooled down to room temperature and diluted with 40 ml of water and extracted with EtOAc (three times). The two layers were separated and the organic layer was dried over anhydrous sodium sulphate, filtered and evaporated to obtain crude product as a brown coloured liquid. It was purified by distillation under reduced pressure (vapour temperature 120-130° C.) 2 mm of Hg to obtain desired dolicholactam as a pure pale yellow solid in 6.2 g quantity (65% yield) with a purity of >98% by HPLC. $^1$H NMR ($CDCl_3$, δ in ppm): 7.0 (s, 1H), 5.6 (s, 1H), 2.8-2.6 (q, 1H), 2.4-2.28 (m, 2H), 2.1-2.0 (m, 1H), 1.9-1.8 (m, 1H), 1.7 (s, 3H), 1.62 (s, 3H), 1.5 (m, 1H); Mass m/Z (ES+): 166.2 ($M^+$+H).

N-propyl dolicho-C-lactam 4a: An oven dried 500 ml two-necked round bottom flask was cooled to room temperature under a stream of nitrogen, 30% KH was taken in to this flask and washed with 25 ml of hexanes three times to remove the mineral oil and was added 280 ml of THF into this flask under nitrogen and cooled the reaction mixture to 0° C. THF (in 20 ml) solution of dolicholactam (10 g, 60.52 mmol) was separately prepared and was added to this flask drop-wise. After the mixture was stirred for 0.5 h at the same temperature 1-Iodopropane (12.9 ml, 133.14 mmol) was added slowly dropwise for a period of 5 min, and the reaction mixture was stirred for another 0.5 h at 0° C. and then was stirred at RT for 2 h. As a work-up the reaction was quenched by the addition of 10% aq. sodium bisulfite (100 ml) and extracted with DCM (three times). The two layers were separated and the organic layer was dried over anhydrous sodium sulphate, filtered and evaporated to obtain crude product which was purified by silica-gel column chromatography using 15% EtOAc/hexane as an eluent to obtain desired N-propyl dolicho-C-lactam as a yellow liquid in 11 g quantity (79% yield) with 99.5% purity by HPLC. $^1$H NMR ($CDCl_3$, δ in ppm): 5.6 (s, 1H), 3.6-3.4 (m, 1H), 3.3-3.2 (m, 1H), 2.8-2.6 (q, 1H), 2.3-2.2 (m, 2H), 2.0 (m, 1H), 1.8 (m, 1H), 1.6-1.4 (m, 7H), 1.2 (d, 3H), 0.9 (t, 3H); Mass m/Z (ES+): 208.5 ($M^+$+H).

Free Choice Assay against mosquitoes (compact repellency): Mosquitoes used were nulliparous female *Aedes aegypti* (Red eye Liverpool strain). They were laboratory-reared and maintained at 27° C. and 80% RH under a photoperiod of 12:12 (L:D) h by using standard mosquito rearing procedures (Rutledge, C. C., et al., J. Med. Entomol., 14: 536-541 (1978)). Larvae were fed a diet of ground tropical fish flakes and adults were fed a 10% sucrose solution. Adult female mosquitoes used for experimentation were between 5 and 15 d old and starved (provided only water) for 24 h before testing.

The test system consisted of a mosquito blood-feeder, a constant-temperature water circulator (to maintain the temperature of the blood at 37° C.) and a specially designed cage. The mosquito blood-feeder contained five circular blood reservoirs, each of which was filled with outdated human blood titrated with adenosine triphosphate. The wells were then covered with sausage membrane and secured using high vacuum grease. Absolute ethanol was used as a solvent and diluent for candidate repellents. Each diluted repellent solution was then randomly applied to the membrane surface at concentrations of 0.02, 0.04, 0.08 and 0.16 mg/cm$^2$. A separate membrane covered well served as a control. 250 mosquitoes were exposed to the treated membranes on the blood reservoirs ad libitum by opening the sliding door in the floor of the test cage. The number of mosquitoes feeding on each well was counted and noted at two-minute intervals for 20 minutes using the total number of feeding mosquitoes as a response. Each test was replicated for a minimum of four times to obtain a statistically valid sample size for analysis. The median effective dose to repel 50% of the mosquito test population was then calculated by the method of Goldstein (Goldstein, A., et al., 1974. Principles of Drug Action: The Basis of Pharmacology, 2nd ed., John Wiley and Sons, New York, N.Y., 854 p) (chemical sensitivity levels calculated from the dose-response regression equation) for single curves with graded responses. Significant differences were then determined by comparing the 95% confidence level among effective doses. In primary in vitro screening, all the lactam analogs surprisingly showed either equal or better feeding deterrent activity compared to DEET against *Aedes aegypti* females (see Table 1).

Feeding Deterrency assay utilising K&D module (Klun, J. A., and M. Debboun, J. Med. Entomol., 37: 177-181 (2000); Klun, J. A., et al., 40: 293-299 (2003)): Test compounds were bioassayed for their feeding deterrency against *Aedes aegypti* females in K&D module assay. Each compound was evaluated in 12 replicates against 5 female mosquitoes. Feeding deterrency was evaluated as proportion feeding. Mean numbers are presented in table 2 and chart [?]. Ethanol was used as control.

As shown in table 2, the efficacy of N-substituted lactams as feeding deterrents were surprisingly better than that of their botanical precursors (verbenone, camphor).

In primary in vitro screening, all the lactam analogs surprisingly showed either equal or better feeding deterrent activity compared to DEET against *Aedes aegypti* females (see below).

Sand Fly (*Phlebotomus papatasi*) blood-feeding assay for testing repellents and feeding deterrents: A pig intestine-based membrane feeing system (Watnaporn, D., et al., Proceedings of VIIIth Sir Dorabjee Tata International Symposium: Arthropod born viral infections-Current status and research, Pages 417-424, 2008) has been used for blood-feeding of female sand flies in colony maintenance. The same technique has been used for testing repellency and antifeeding effects of several new compounds. A circular area of the fabric mesh on top of the test container that matches the size of the glass feeder was treated with the test compound by applying the test solution using a Q-tip. After a group of 30 females and 15 males was placed into the test container, a glass feeder filled with cow blood was placed on top of the treated area in the center of the fabric mesh that was secured on top of the container. Sand flies were allowed to feed for 2 h before the number of blood-fed females was in each feeding container counted.

Female sand flies in the untreated control achieved a 32% to 61% blood feeding rate during the test period (2 h) when a group of 30 females and 15 males was placed in a feeding pot and fed through a fine mesh screen using an artificial membrane feeding system (Table 1 [?]). Surprisingly dolicholactam (3) was more effective than dolicholactone and N-propyl dolicholactam (3a) was more effective than dolicholactam. The most effective compounds surprisingly were D-Camphor Lactam (1) and n-propyl D-Camphor Lactam (1a), both compounds surprisingly achieved >90% repellency at a concentration as low as 0.00001% (or 0.001 µg/cm$^2$). See Table 3.

Tick repellency: Vertical filter paper bioassay against adult lone star ticks, *Amblyomma americanum*, and nymphs was conducted with selected lactams, lactones and ketones. Adult ticks were exposed 10-15 minutes after application of the candidate compounds. Repellency was measured in % repelled from the treated surface at various concentrations. See Table 4. All the N-substituted lactams surprisingly exhibited higher repellency at 2000 and 500 ug amount compared to DEET. These lactams also surprisingly exhibited repellency at 125 and 64 ug concentrations where DEET failed to repel ticks. Surprisingly one of the cyclic ketone (7a) repelled adult ticks at lowest concentration (31 ug) in filter paper bioassay.

The surprising advantages of newly identified application of lactams described herein include crystalline solid compounds (mp 60-150° C.), ease of commercial synthesis (ammonium hydroxide and dehydration), economical, no irritating odors and low vapor pressure (better for formulation), and spectrum of putative toxic effects may be limited (based on chemistry).

All of the references cited herein are incorporated by reference in their entirety. Also incorporated by reference in their entirety are the following references: Auda, H., et al., J. Am. Chem. Soc., 89: 2476-2482 (1967); Birkett, M. A., and J. A., Pickett, Phytochemistry, 62: 651-656 (2003); Chauhan, K. R., et al., Tetrahedron Lett., 45: 3339-3340 (2004); Chauhan, K. R., et al., J. Med. Entomol., 42(4): 643-646 (2005); Dawson, G. W., et al., Bioorg. Med. Chem., 4: 351-361 (1996); Eisenbraun, E. J., et al., J. Org. Chem., 53: 3968-3972 (1988); Hooper A. M., et al, J. Chem. Ecol., 28: 849-864 (2002); Li, Y., and P. A. Jacobi, Org. Lett., 5: 701-704 (2003); Liblikas I., et al., J. Nat. Prod., 68: 886-890 (2005); Lichtenthaler, F. W., Carbohydrate Synthons in Natural Product Synthesis, ACS Symposium Series 841, pp 47-83 (2003); Meinwald, J., et al., Proc. Natl. Acad. Sci., 74(6): 2189-2193 (1977); Mulzer, J., et al., J. Am. Chem. Soc., 119: 5512-5518 (1997); Taylor, W. I., and A. Battersby, Cyclopentanoid Terpene Derivatives, Marcel Dekker, New York, 1969.

Also incorporated by reference in their entirety are the following U.S. Patent Application Publications: 20060121134 (Chauhan et al.); 20030138471 (Coats et al.); 20050112166 (Hallahan); 20050069568 (Hallahan); 20040127553 (Hallahan); 20030235601 (Hallahan);

Also incorporated by reference in their entirety are the following U.S. patents: U.S. Pat. No. 6,524,605 (Coats et al.); U.S. Pat. No. 6,572,841 (Klun et al.); U.S. Pat. No. 7,067,678 (Scialdone).

Thus, in view of the above, the present invention concerns (in part) the following:

A composition, comprising (or consisting essentially of or consisting of) at least one compound selected from the group consisting of

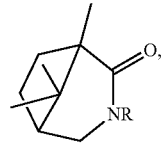

-continued

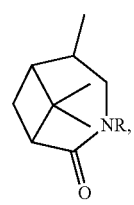

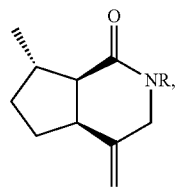

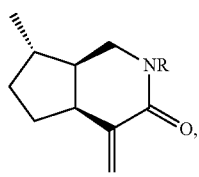

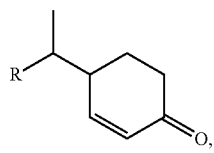

and mixtures thereof, where R is H, C1 to C10 alkyl, or C1 to C10 alkenyl, and optionally a carrier.

The above composition, wherein said composition contains

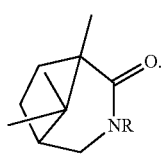

The above composition, wherein said composition does not contain

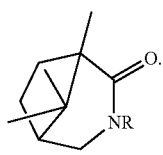

The above composition, wherein said composition contains

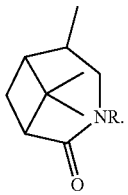

The above composition, wherein said composition does not contain

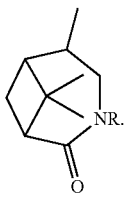

The above composition, wherein said composition contains

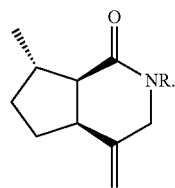

The above composition, wherein said composition does not contain

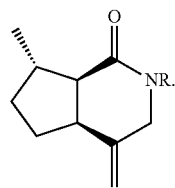

The above composition, wherein said composition contains

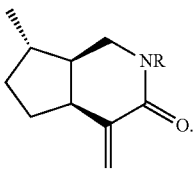

The above composition, wherein said composition does not contain

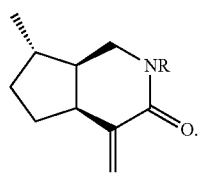

4

The above composition, wherein said composition contains

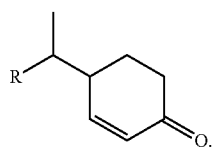

7

The above composition, wherein said composition does not contain

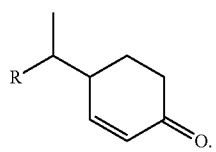

7

The above composition, wherein said composition further contains

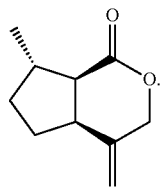

5

The above composition, wherein said composition does not further contain

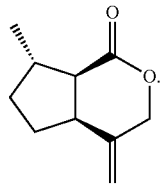

5

The above composition, wherein said composition further contains

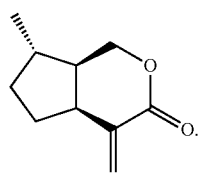

6

The above composition, wherein said composition does not further contain

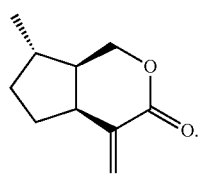

6

Regarding the above compositions, as used herein the term "at least two" optionally includes, for example, at least two compounds selected from compounds 1, 2, 3, 4, and 7, or one compound (two versions) where the R is different (e.g., compound 1 where R is H and compound 1 where R is C1 to C10 alkyl). The same applies to "at least three", and "at least four".

A method for repelling blood-sucking and biting insects, ticks and mites, said method comprising (or consisting essentially of or consisting of) treating an object or area with a blood-sucking and biting insects, ticks and mites repelling effective amount of a composition comprising at least one compound selected from the group consisting of

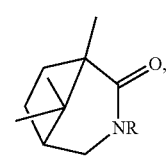

1

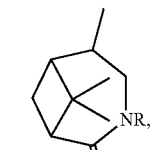

2

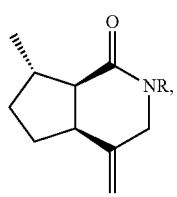

3

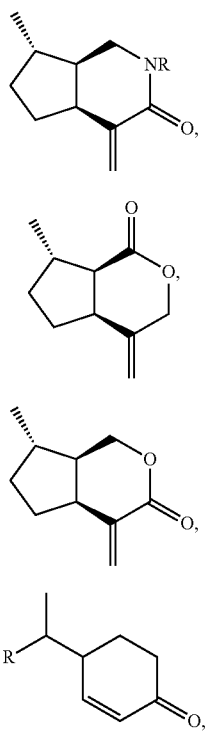

and mixtures thereof, where R is H, C1 to C10 alkyl, or C1 to C10 alkenyl; and optionally a carrier.

The above method, wherein said composition contains

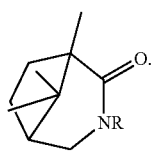

The above method, wherein said composition does not contain

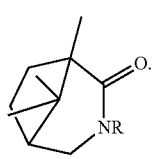

The above method, wherein said composition contains

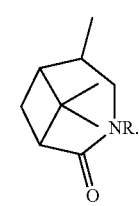

The above method, wherein said composition does not contain

The above method, wherein said composition contains

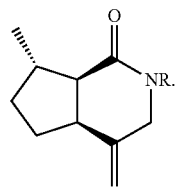

The above method, wherein said composition does not contain

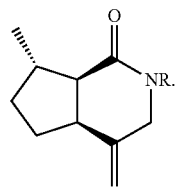

The above method, wherein said composition contains

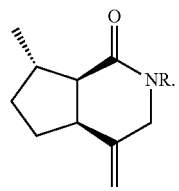

The above method, wherein said composition does not contain

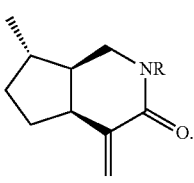

The above method, wherein said composition contains

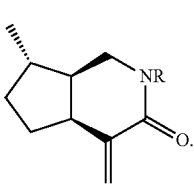

The above method, wherein said composition contains

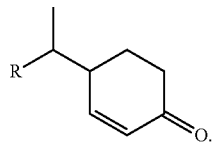

The above method, wherein said composition does not contain

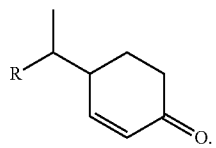

The above method, wherein said composition contains

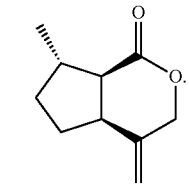

The above method, wherein said composition does not contain

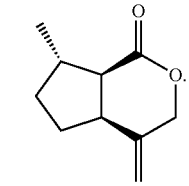

The above method, wherein said composition contains

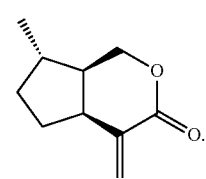

The above method, wherein said composition does not contain

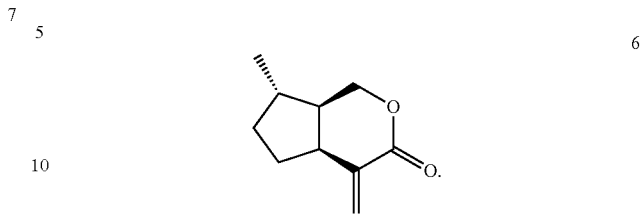

Regarding the above methods, as used herein, the term "at least two" optionally includes, for example, at least two compounds selected from compounds 1, 2, 3, 4, 5, 6 and 7, or one compound (two versions) where the R is different (e.g., compound 1 where R is H and compound 1 where R is C1 to C10 alkyl). The same rationale applies to "at least three", "at least four", "at least five", and "at least six".

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1 feeding deterrence assay in glove box against mosquitoes (*Aedes aegypti*)

| Compound | $EC_{50}$ (vg) | $EC_{95}$ (vg) | $R^2$ |
|---|---|---|---|
| N-propyl C-lactam | 0.0282 | 0.102 | 0.9989 |
| (1a) | (0.0173 to 0.0382) | (0.090 to 0.1134) | |
| N-propyl d-lactam | 0.0317 | 0.117 | 0.9989 |
| (3a) | (0.0233 to 0.0419) | (0.1102 to 0.1209) | |
| C-lactam (1) | 0.0355 | 0.166 | 0.9989 |
| | (0.0231 to 0.0397) | (0.1132 to 0.1839) | |
| N-propyl V-lactam | 0.0561 | 0.264 | 0.9989 |
| (2a) | (0.0311 to 0.0607) | (0.2202 to 0.2777) | |
| d-lactam (3) | 0.0322 | 0.173 | 0.9989 |
| | (0.0196 to 0.037) | (0.1507 to 0.2031) | |
| DEET | 0.0306 | 0.189 | 0.9989 |
| | (0.024 to 0.0366) | (0.1333 to 0.1830) | |

TABLE 2

Feeding deterrence assay at 25 nmol\ $cm^2$ concentrations (K&D module).

| Compound | total Bites\120 | mean bites\6 | % not biting |
|---|---|---|---|
| Ethanol | 76 | 3.8 | 37 |
| DEET | 8 | 0.4 | 94 |
| (1) Camphor lactam | 11 | 0.55 | 91 |
| (1a) N-propyl camphor lactam | 5 | 0.25 | 96 |
| (2a) N-propyl DH verbeno lactam | 10 | 0.5 | 92 |
| (3) Dolicho (C) lactam | 10 | 0.5 | 92 |
| (3a) N-propyl dolicho-C-lactam | 3 | 0.15 | 98 |
| (5) Dolicholactone (C) | 14 | 0.7 | 89 |
| (6) Dolicho lactone (D) | 16 | 0.8 | 87 |

TABLE 3

| Concentration | Mean % Feeding | stdev | stderr | Mean % Inhibition | stdev | stderr |
|---|---|---|---|---|---|---|
| Camphor Lactam n = 3 | | | | | | |
| Control | 37.8 | 10.2 | 5.9 | | | |
| 0.00001% | 6.7 | 0.0 | 0.0 | 90.9 | 0.0 | 0.0 |
| 0.0001% | 3.3 | 3.3 | 1.9 | 95.5 | 4.5 | 2.6 |
| 0.001% | 2.2 | 1.9 | 1.1 | 97.0 | 2.6 | 1.5 |
| 0.01% | 0.0 | 0.0 | 0.0 | 100.0 | 0.0 | 0.0 |
| n-propyl camphor lactam n = 3 | | | | | | |
| Control | 32.2 | 8.4 | 4.8 | | | |
| 0.00001% | 5.6 | 1.9 | 1.1 | 92.4 | 2.6 | 1.5 |
| 0.0001% | 6.7 | 6.7 | 3.8 | 90.9 | 9.1 | 5.2 |
| 0.001% | 1.1 | 1.9 | 1.1 | 98.5 | 2.6 | 1.5 |
| 0.01% | 0.0 | 0.0 | 0.0 | 100.0 | 0.0 | 0.0 |
| n-propyl dolicho lactam n = 3 | | | | | | |
| Control | 37.8 | 19.2 | 11.1 | | | |
| 0.001% | 25.6 | 21.2 | 12.2 | 65.1 | 28.9 | 16.7 |
| 0.01% | 17.8 | 22.2 | 12.8 | 75.8 | 30.3 | 17.5 |
| 0.02% | 8.9 | 7.7 | 4.4 | 87.9 | 10.5 | 6.1 |
| 0.04% | 5.6 | 5.1 | 2.9 | 92.4 | 6.9 | 4.0 |

TABLE 4

| Compound | Conc. (ug) | % repelled | # of ticks |
|---|---|---|---|
| (1) camphor lactam | 2000 | 73.3 | 30 |
| | 500 | 66.7 | 30 |
| | 125 | 26.7 | 30 |
| (1a) N-propyl camphor lactam | 2000 | 93.3 | 30 |
| | 500 | 100 | 30 |
| | 125 | 26.7 | 30 |
| (3a) N-propyl dolicho lactam | 2000 | 100 | 30 |
| | 500 | 100 | 30 |
| | 125 | 83.6 | 30 |
| | 63 | 20 | 30 |
| (7a) 4-(1,5-Dimethylhex-4-enyl) cyclohex-2-en-1-one | 2000 | 82.5 | 30 |
| | 500 | 96.7 | 30 |
| | 125 | 73.3 | 30 |
| | 63 | 53.3 | 30 |
| | 31 | 20 | 30 |
| DEET | 2000 | 95.7 | 70 |
| | 500 | 68.3 | 60 |
| | 125 | 5 | 40 |
| Acetone control | 0 | 7.9 | 190 |

We claim:

1. A composition, comprising at least two compounds selected from the group consisting of

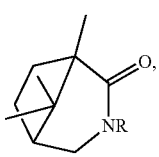

1

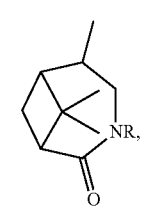

2

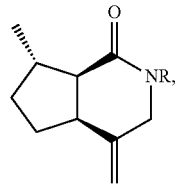

3

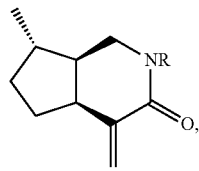

4

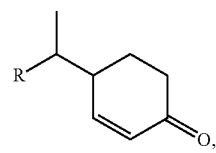

7 and mixtures thereof, where R is H, C1 to C10 alkyl, or C1 to C10 alkenyl, and optionally a carrier.

2. The composition according to claim 1, wherein said composition comprises at least three compounds selected from the group consisting of

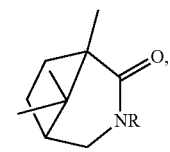

1

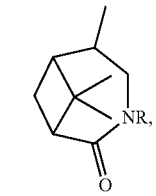

2

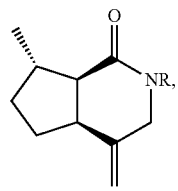

3

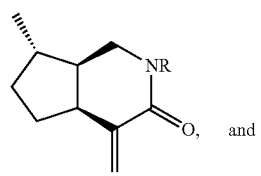

4 and

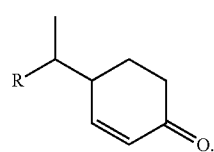

3. The composition according to claim 1, wherein said composition comprises at least four compounds selected from the group consisting of

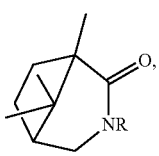

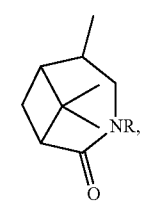

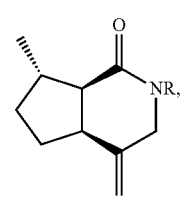

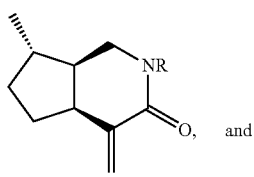

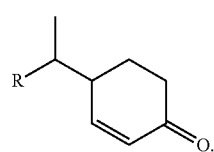

and

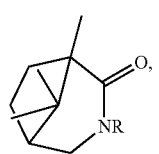

4. The composition according to claim 1, wherein said composition comprises

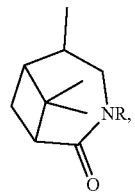

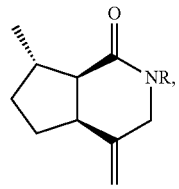

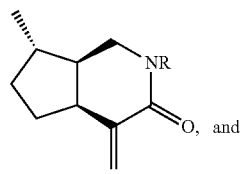

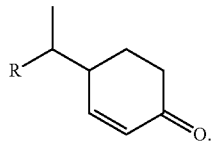

and

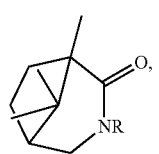

5. The composition according to claim 1, wherein said composition further comprises at least one compound selected from the group consisting of

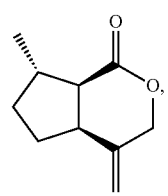

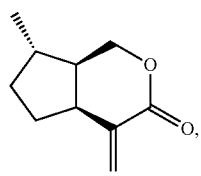

and mixtures thereof.

6. The composition according to claim 1, wherein said composition further comprises

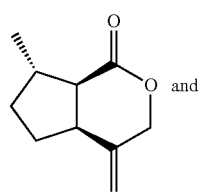

and

-continued

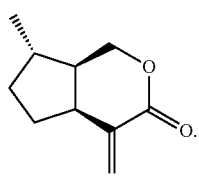
6

7. A method for repelling blood-sucking and biting insects, ticks and mites, said method comprising treating an object or area with a blood-sucking and biting insects, ticks and mites repelling effective amount of a composition comprising at least one compound selected from the group consisting of -continued

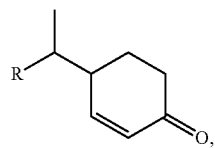
7 and mixtures thereof, where R is H, C1 to C10 alkyl, or C1 to C10 alkenyl; and optionally a carrier.

8. The method according to claim 7, wherein said composition comprises at least two compounds selected from the group consisting of

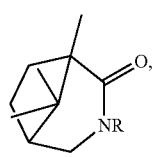
1

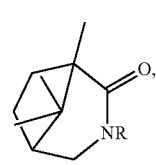
1

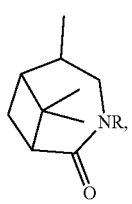
2

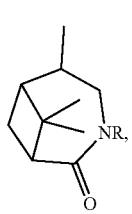
2

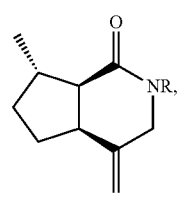
3

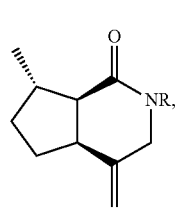
3

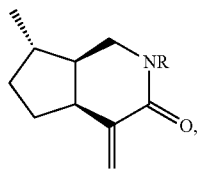
4

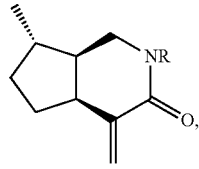
4

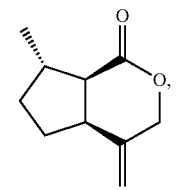
5

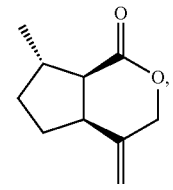
5

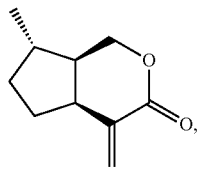
6

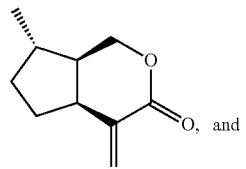
6, and

-continued
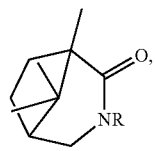
7
9. The method according to claim 7, wherein said composition comprises at least three compounds selected from the group consisting of
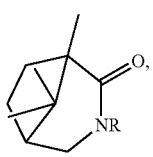
1
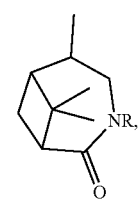
2
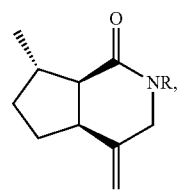
3
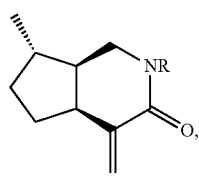
4
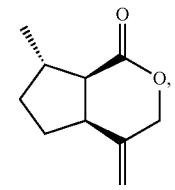
5
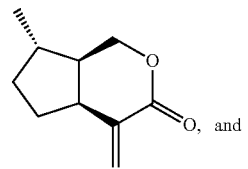
6
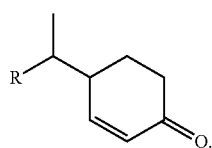
7
10. The method according to claim 7, wherein said composition comprises at least four compounds selected from the group consisting of
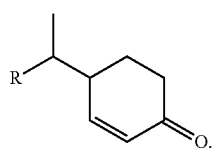
1
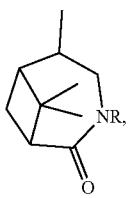
2
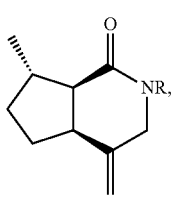
3
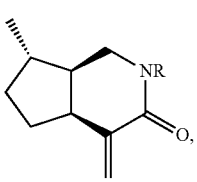
4
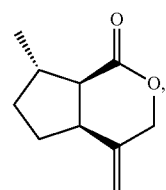
5
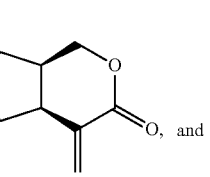
6
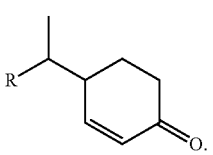
7

11. The method according to claim 7, wherein said composition comprises at least five compounds selected from the group consisting of
1
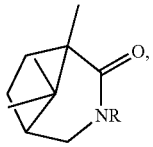
2
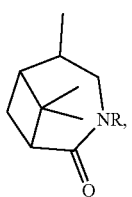
3
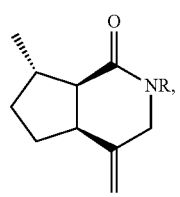
4
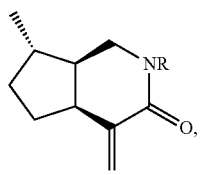
5
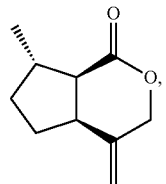
6
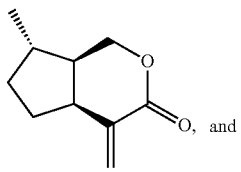, and
7
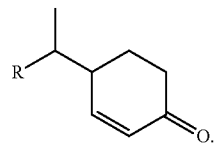
12. The method according to claim 7, wherein said composition comprises at least six compounds selected from the group consisting of
1
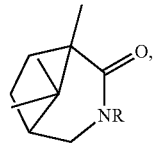
2
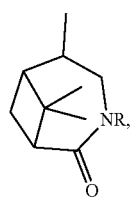
3
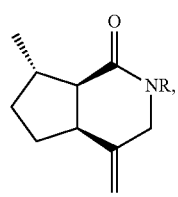
4
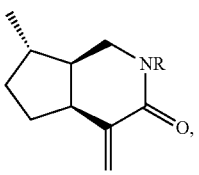
5
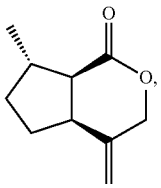
6
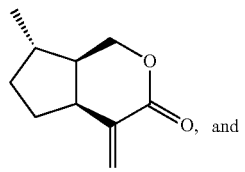, and
7
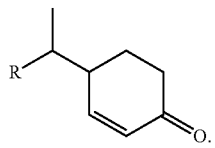

13. The method according to claim 7, wherein said composition comprises
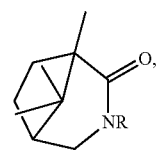
1
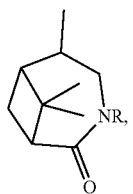
2
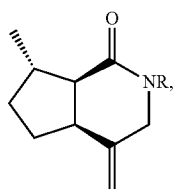
3
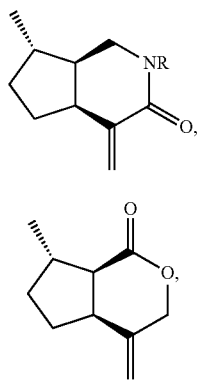
4
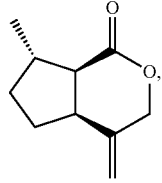
5
-continued
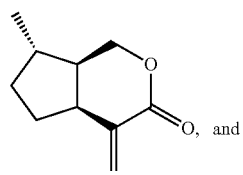
6
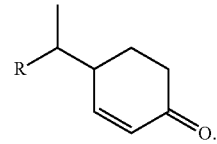
7
14. A composition, comprising
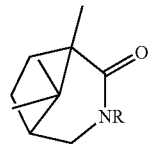
where R is C2 to C10 alkyl or C1 to C10 alkenyl, and optionally a carrier.
15. A composition, comprising
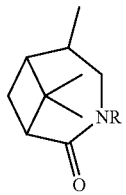
where R is C2 to C10 alkyl or C1 to C10 alkenyl, and optionally a carrier.
* * * * *